(12) United States Patent
Zhang et al.

(10) Patent No.: US 8,662,757 B2
(45) Date of Patent: Mar. 4, 2014

(54) SELF ADJUSTING BEARING USED ON CT GANTRY

(75) Inventors: Xiaoyan Zhang, Beijing (CN); Hailiang Liu, Beijing (CN); Zhuo Liu, Beijing (CN); Xuyong Yang, Beijing (CN); Xueli Wang, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 151 days.

(21) Appl. No.: 13/315,090

(22) Filed: Dec. 8, 2011

(65) Prior Publication Data

US 2012/0148013 A1 Jun. 14, 2012

(30) Foreign Application Priority Data

Dec. 10, 2010 (CN) .......................... 2010 1 0602819

(51) Int. Cl.
*F16C 13/00* (2006.01)

(52) U.S. Cl.
USPC ............................................... 384/549

(58) Field of Classification Search
USPC ............ 384/57, 58, 247, 256, 257, 549, 558, 384/583, 616; 378/4, 15, 196, 197
See application file for complete search history.

(56) References Cited

U.S. PATENT DOCUMENTS

| | | | | |
|---|---|---|---|---|
| 2,501,166 A * | 3/1950 | Fraser et al. | .................. | 241/252 |
| 2,589,619 A * | 3/1952 | Leef | .............................. | 366/232 |
| 3,517,915 A * | 6/1970 | Deynat et al. | ................. | 384/549 |
| 3,836,103 A * | 9/1974 | Retali et al. | .................... | 248/130 |
| 4,394,738 A * | 7/1983 | Wagner | ............................. | 378/4 |
| 4,552,508 A * | 11/1985 | Reid | .............................. | 415/72 |
| 4,592,694 A * | 6/1986 | Johnson | ........................ | 414/534 |
| 4,977,586 A * | 12/1990 | Curry | .............................. | 378/61 |
| 5,473,657 A * | 12/1995 | McKenna | ......................... | 378/4 |
| 6,337,894 B1 | 1/2002 | Tybinkowski et al. | | |
| 6,447,289 B1 * | 9/2002 | Boyne et al. | .................. | 432/118 |
| 2002/0146088 A1 * | 10/2002 | Riemer et al. | ..................... | 378/4 |
| 2004/0062343 A1 * | 4/2004 | Brunnett et al. | ................ | 378/15 |
| 2005/0220382 A1 | 10/2005 | Katou et al. | | |
| 2010/0195949 A1 | 8/2010 | Yagi et al. | | |
| 2011/0109030 A1 * | 5/2011 | Flaig | .............................. | 269/55 |

\* cited by examiner

*Primary Examiner* — James Pilkington
(74) *Attorney, Agent, or Firm* — Armstong Teasdale LLP (57) ABSTRACT

A self adjusting bearing for use on a CT gantry is provided. The self adjusting bearing is configured to be mounted on a main frame of the CT gantry and is configured to support a rotating base of the CT gantry wherein the self adjusting bearing includes a roller, a first component, and a second component, the roller is configured to support the rotating base and is rotatably mounted on the first component, the second component is configured to be mounted on the main frame, and the first component and the second component are configured to rotatably engage each other such that they can rotate relative to each other during the mounting of the self adjusting bearing.

19 Claims, 9 Drawing Sheets

SELF ADJUSTING BEARING USED ON CT GANTRY

CROSS-REFERENCE TO RELATED APPLICATIONS

This application claims the benefit of Chinese Patent Application No. 201010602819.7 filed Dec. 10, 2010, which is hereby incorporated by reference in its entirety.

BACKGROUND OF THE INVENTION

The present invention relates to a CT gantry, and more specifically to a self adjusting bearing used on a CT gantry.

Current CT gantries have a main bearing, a big pulley and a rotating base for support and rotation of all rotating parts in the CT gantry. The main bearing is one of the most critical mechanical parts for the CT gantry.

However, the main bearing of a current CT gantry has many drawbacks. First, the current CT main bearing is expensive, which increases the total cost of the ICV in the CT system. Second, the CT main bearing is a slewing bearing with a very complicated structure. Most of the bearings are purchased from abroad, which have a long lead time, and are difficult for localization. Third, the main bearing and the rotating base are in a cantilever beam structure, which creates a significant overturn moment of the main bearing. This results in a high failure rate and low resistance for vibration and shock during shipment and handling of the main bearing. Finally, the failure of the main bearing, such as noise and screw skip issues, in the field leads to the replacement of the whole gantry or even CT system, which will necessarily increase service expenses and customer complaints.

U.S. Pat. No. 5,473,657 discloses a bearing assembly for supporting the rotating base. The bearing assembly is composed of a plurality of supporting rollers, which are in contact with an outer periphery of the rotating base. The supporting rollers may be made of a resilient material to dampen vibration transfer from the frame to the rotating base. These supporting rollers have a cylindrical shape and thus can limit the movement of the rotating base in the scanning plane defined by X-Y. However, these supporting rollers having a cylindrical shape cannot limit the rotating base's movement in the Z-direction perpendicular to the scanning plane. Therefore, three additional resilient roller pairs are used for contacting the side edge of the rotating base so as to limit the rotating base's movement in the lateral direction, namely, the Z direction.

When the rotating base expands or contracts in the scanning plane as a result of temperature changes, a sliding friction will occur between the three pairs of resilient rollers contacting the side edge and the rotating base. This will increase material wear of the resilient rollers and the rotating base.

SUMMARY OF THE INVENTION

In view of the bearing in existing CT gantries, a self adjusting bearing for use on a CT gantry is described herein.

According to one aspect, there is provided a self adjusting bearing for use on a CT gantry. The self adjusting bearing is mounted on a main frame of the CT gantry and supports a rotating base of the CT gantry. The self adjusting bearing has a roller, a first component, and a second component. The roller supports the rotating base and is mounted on the first component. The second component is mounted on the main frame. The first component and the second component can rotatably match with each other so that they can rotate relative to each other during the mounting of the self adjusting bearing.

According to another aspect, there is provided a CT gantry having a main frame, a rotating base, and a self adjusting bearing mentioned above. The self adjusting bearing is mounted on the main frame and supports the rotating base of the CT gantry.

According to a further aspect, there is provided a CT system having the above-mentioned self adjusting bearing or CT gantry.

The self adjusting bearing can provide many benefits. Firstly, it will significantly reduce cost of the CT system by using small self adjusting bearings to replace a big slewing bearing. Secondly, the self adjusting bearings have a simple structure and can cooperate with common bearings in industry. These common bearings can be purchased from local or global suppliers easily. Thirdly, the self adjusting bearing eliminates an overturn moment in the existing main bearing and as a result will have a lower failure rate. Finally, in case of bearing failure, the self adjusting bearings can be replaced in the field, thus eliminating the need to replace the whole gantry or CT system.

The rotating base described herein can serve as a pulley for engaging the driving belt for driving the rotating base, as a rail for guiding the bearings, and as a base for fixing rotating components.

These and other advantages and features will become more apparent from the description below in connection with the drawings.

BRIEF DESCRIPTION OF THE DRAWINGS

The features of the embodiments described herein will become clearer when the following detailed description of the exemplary embodiments is read with reference to the accompanying drawings in which like reference numerals represent like parts throughout the: drawings.

DETAILED DESCRIPTION OF THE INVENTION

The following detailed description is provided with reference to figures which schematically show exemplary embodiments. These embodiments are described in sufficient detail as to enable those skilled in the art to carry them out and to make structural changes through combinations thereof or with other embodiments, without departing from the scope of the embodiments described herein. Therefore, the following detailed description shall not be construed as limiting the present invention.

As used herein, unless otherwise indicated, the term "a" or "an" indicates one or more, and the terms "comprising", "including", and "having" indicate the existence of further element(s) in addition to those listed.

Figure 1:
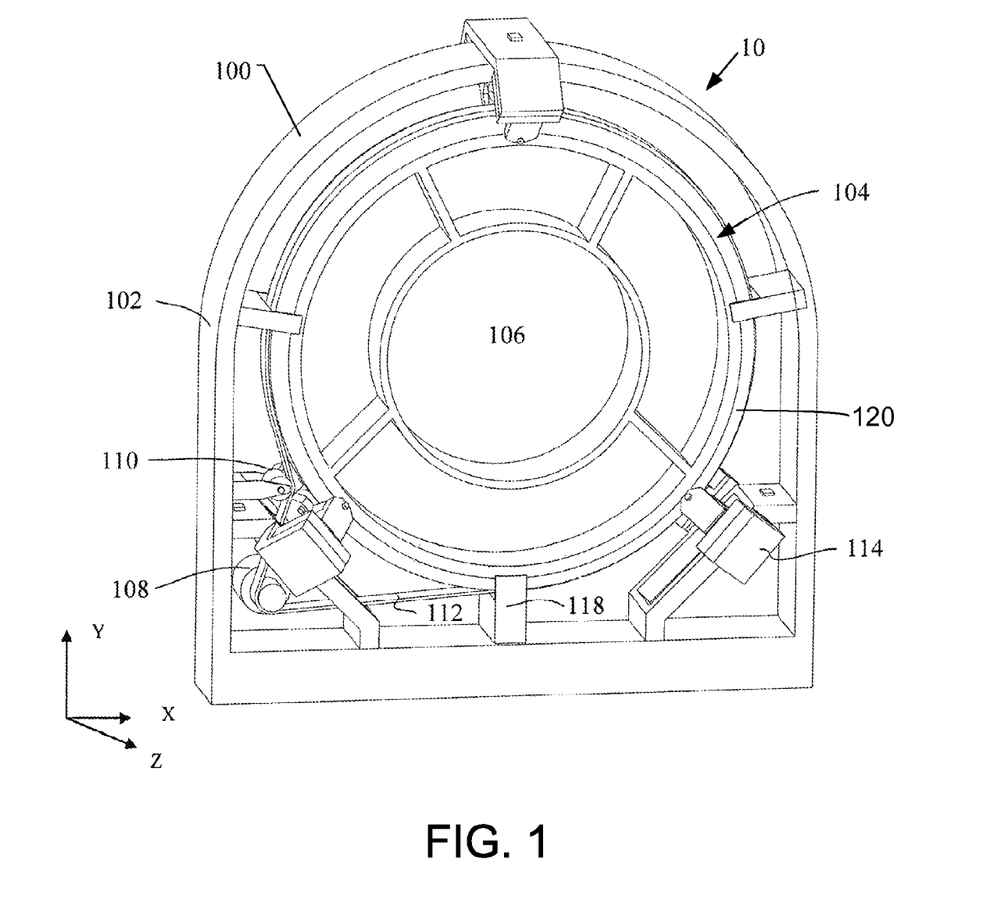
FIG. 1 is a perspective view of an exemplary CT system.

FIG. 1 is a perspective view of a CT system 10 according to an exemplary embodiment. The CT system 10 has a CT gantry 100 including a main frame 102 and a rotating base 104. The rotating base 104 has a scanning chamber 106 for receiving a human body to be scanned by the CT system, and can rotate around a center axis in a scanning plane X-Y. The rotating base 104 is supported by the main frame 102 via self adjusting bearings 200 such that it can rotate freely. A rotating driver 108 is mounted on the main frame 102 or any other suitable positions, and drives a driving belt 112 that engages an outer periphery 120 of the rotating base 104. A tension pulley 110 is also mounted on the main frame 102 or any other suitable positions for tightening the driving belt 112. When the driving belt 112 is driven by the rotating driver 108, the rotating base 104 is caused to rotate. The tension pulley 110 tightens the driving belt 112 such that a sufficient friction is generated between the driving belt 112 and the rotating base 104 and no slipping will occur.

Figure 2:
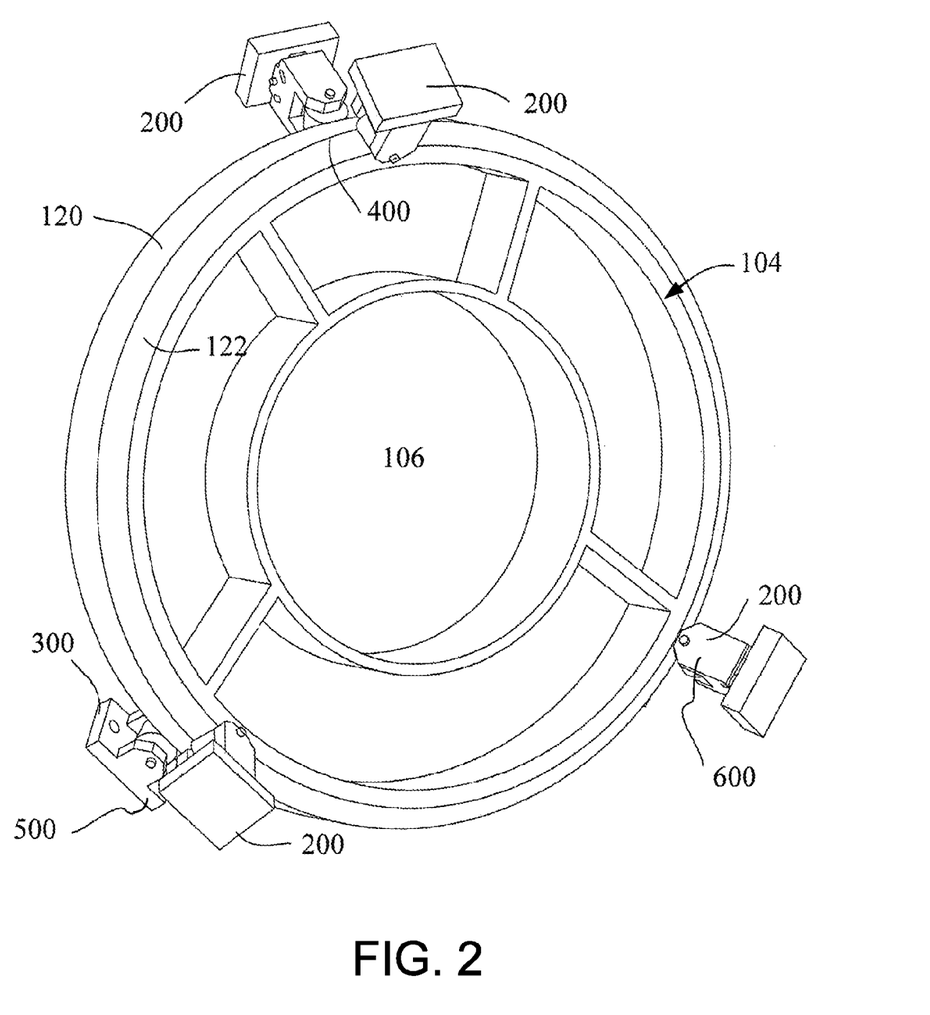
FIG. 2 is a perspective view of a self adjusting bearing and a rotating base that may be used with the CT system shown in FIG. 1.

FIG. 2 shows the way in which the rotating base 104 of the CT gantry 100 is supported by self adjusting bearings 200. It shall be noted that fixed type bearings 300 can also be used in the CT gantry 100 for supporting the rotating base 104 in cooperation with self adjusting bearings 200. As shown in FIG. 2, a first bearing couple 400 including two self adjusting bearings 200 disposed at two opposing sides of the rotating base 104 is provided at an upper part of the rotating base 104. In addition, a second bearing couple 500 and a third bearing couple 600, each including a self adjusting bearing 200 and a fixed type bearing 300 at two opposing sides of the rotating base 104, are provided at a lower part of the rotating base 104.

The self adjusting bearings 200 of the second bearing couple 500 and the third bearing couple 600 are disposed at the same side of the rotating base 104. Alternatively, the self adjusting bearings 200 of the second bearing couple 500 and the third bearing couple 600 are disposed at opposing sides of the rotating base 104.

Although three bearing couples (namely, the first bearing couple 400 including two self adjusting bearings 200, the second bearing couple 500 including a self adjusting bearing 200 and a fixed type bearing 300, and the third bearing couple 600 including a self adjusting bearing 200 and a fixed type bearing 300) are shown in FIG. 2, it is possible to include any number of bearing couples other than three. For example, when only two bearing couples are provided, the combination thereof can be a second bearing couple 500 plus a third bearing couple 600, or a first bearing couple 400 plus a second bearing couple 500 or a third bearing couple 600. Besides, it is also possible to include a fixed type bearing couple including two fixed type bearings to replace any of the first bearing couple 400, the second bearing couple 500, and the third bearing couple 600.

In order to provide a stable support for the rotating base 104, the center of gravity of the rotating base 104 is arranged between the second bearing couple 500 and the third bearing couple 600. Besides, the first bearing couple 400 is disposed exactly over the rotation center of the rotating base 104. However, the relative position of the first bearing couple 400, the second bearing couple 500, and the third bearing couple 600 can be adjusted. For example, in the case of four bearing couples, the four bearing couples are spaced evenly from each other by 90 degrees on the periphery of the rotating base 104.

Figure 3:
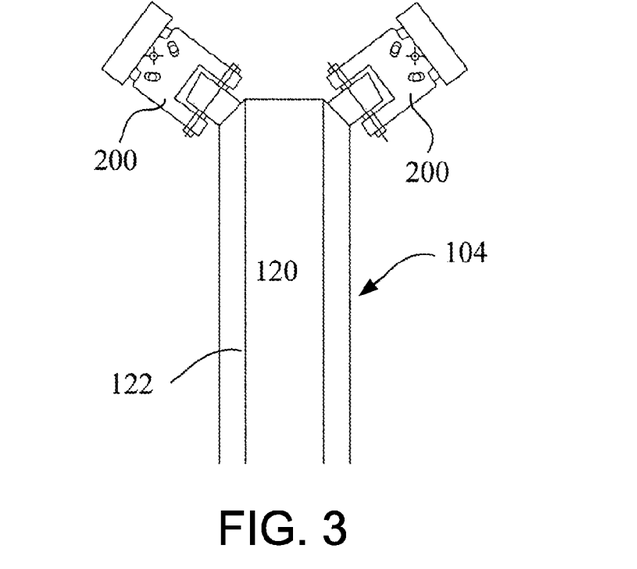
FIG. 3 is a schematic view of a first bearing couple including two self adjusting bearings at an upper part of the rotating base.
Figure 4:
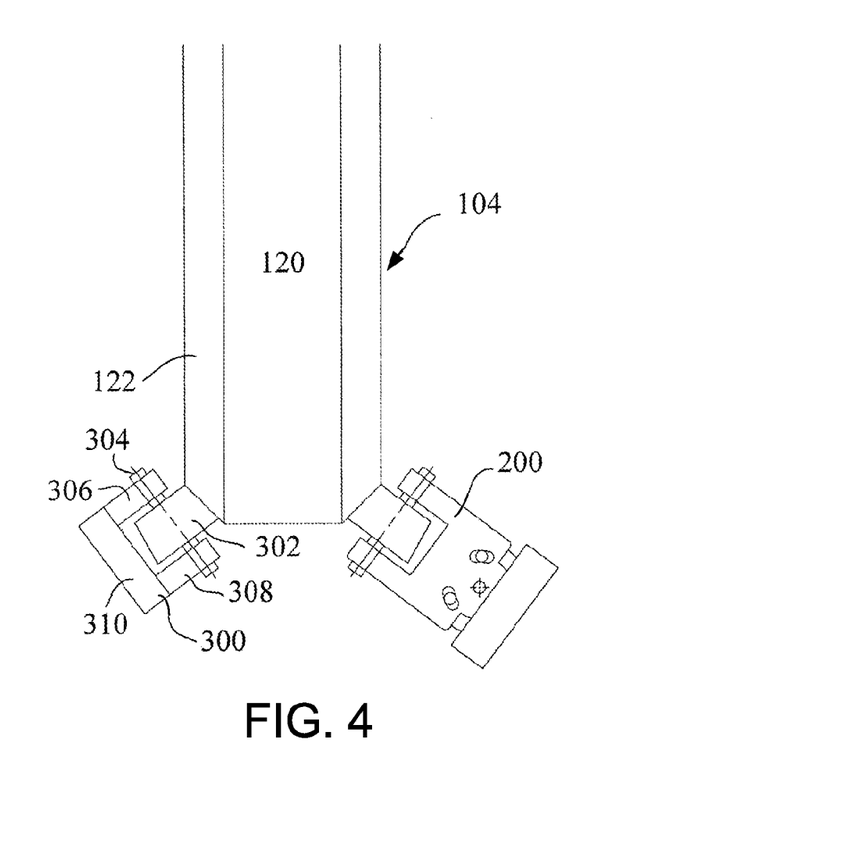
FIG. 4 is a schematic view of a second or a third bearing couple including a self adjusting bearing and a fixed type bearing at a lower part of the rotating base.

FIG. 3 shows a first bearing couple 400 including two self adjusting bearings 200 at an upper part of the rotating base 104, in which the self adjusting bearings 200 are in contact with the chamfers 122 of the rotating base 104. Likewise, FIG. 4 shows a second bearing couple 500 or a third bearing couple 600 including a self adjusting bearing 200 and a fixed type bearing 300 at a lower part of the rotating base 104, in which the self adjusting bearing 200 and the fixed type bearing 300 are in contact with the chamfers 122 of the rotating base 104.

Figure 5:
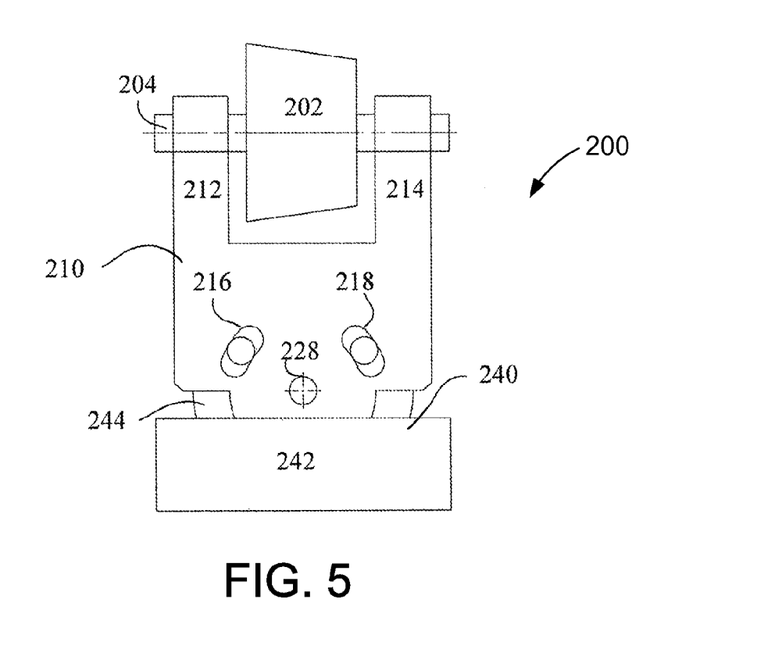
FIG. 5 is a schematic view of an exemplary self adjusting; bearing.

FIG. 5 is a schematic view of a self adjusting bearing 200. The self adjusting bearing 200 includes a roller 202, a convex block 210, and a concave block 240. The roller 202 is rotatably mounted onto the convex block 210 via first mounting piece 204 such that it can rotatably support the rotating base 104 when the rotating base 104 is driven by the rotating driver 108 via the driving belt 112. Similarly, the convex block 210 is rotatably mounted onto the concave block 240 via second mounting piece 226 such that the position of the convex block 210 relative to the concave block 240 can be adjusted during the mounting of the self adjusting bearing 200.

In the embodiment shown in FIG. 5, the second mounting piece 226 is arranged perpendicular or approximately perpendicular to the first mounting piece 204 such that the convex block 210 can rotate relative to the concave block 240 around an axis perpendicular to a longitudinal axis of the roller 202. This makes it possible to adjust the positions of the convex block 210 and the roller 202 in the longitudinal direction of the rotating base 104, namely, the lateral position on the chamfer 122 of the rotating base 104.

Alternatively, the second mounting piece 226 is arranged parallel or approximately parallel to the first mounting piece 204 such that the convex block 210 can rotate relative to the concave block 240 around an axis parallel to a longitudinal axis of the roller 202. This makes it possible to adjust the positions of the convex block 210 and the roller 202 in the scanning plane of the rotating base 104, namely, the circumferential position on the chamfer 122 of the rotating base 104.

Figure 6:
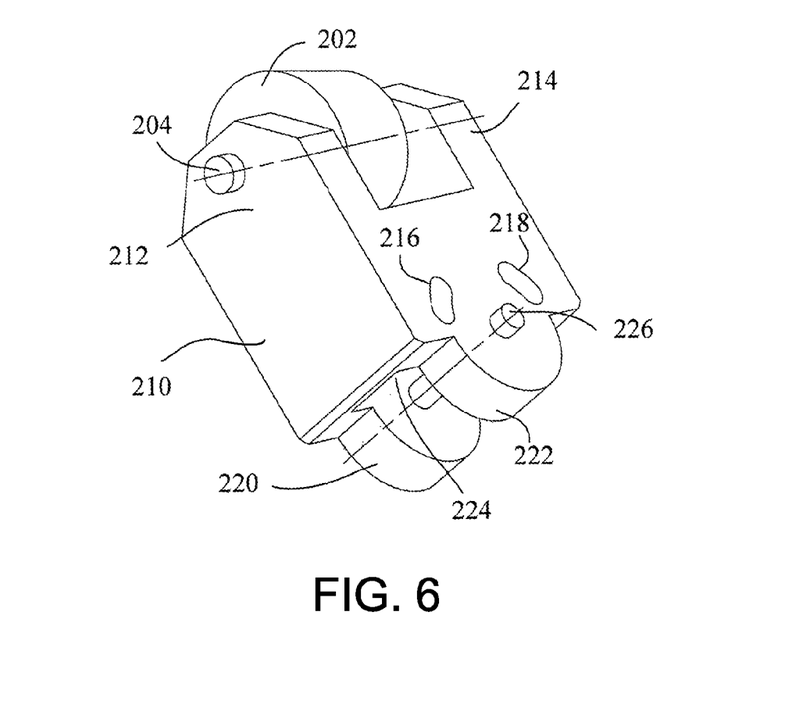
FIG. 6 is a perspective view of a roller and a convex block of a self adjusting bearing.

Referring to FIG. 6, a detailed structure of the convex block 210 is shown. The convex block 210 has a first leg 212 and a second leg 214 at an upper part thereof, and a first protrusion 220 and a second protrusion 222 at a lower part thereof. The roller 202 is rotatably supported between the first leg 212 and the second leg 214 via the first mounting piece 204. The first protrusion 220 and the second protrusion 222 each have a center hole 228 formed therein.

Still referring to FIG. 6, the first protrusion 220 and the second protrusion 222 can be disposed at a plane perpendicular to that of the first leg 212 and the second leg 214. In that case, the second mounting piece 226 is perpendicular to the first mounting piece 204, thereby making it possible to adjust the lateral position of the convex block 210 and the roller 202 on the chamfer 122 of the rotating base 104.

Alternatively, the first protrusion 220 and the second protrusion 222 can be disposed at a plane parallel to that of the first leg 212 and the second leg 214 or even at the same plane as the first leg 212 and the second leg 214. In that case, the second mounting piece 226 will be parallel to the first mounting piece 204, thereby making it possible to adjust the circumferential position of the convex block 210 and the roller 202 on the chamfer 122 of the rotating base 104.

Figure 7:
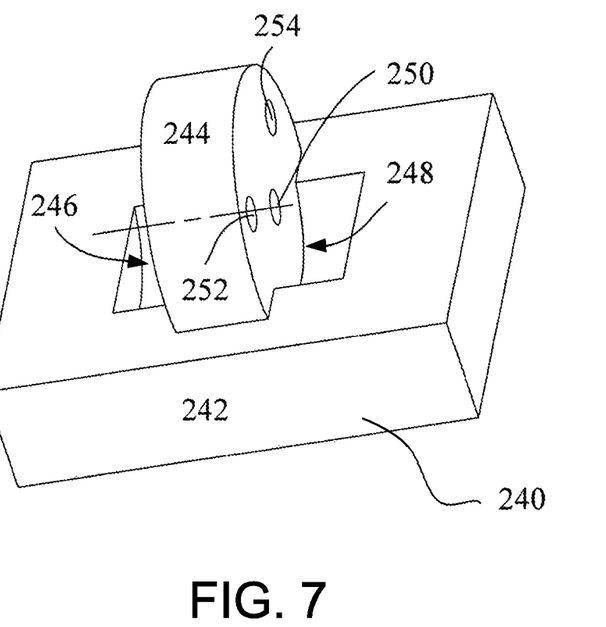
FIG. 7 is a perspective view of a concave block of a self adjusting bearing.

Referring now to FIG. 7, the concave block 240 of the self adjusting bearing 200 has a seat 242 and a third protrusion 244 having a center hole 250. In assembling the convex block 210 and the concave block 240 together, the center holes 228 of the first protrusion 220 and the second protrusion 222 are aligned with the center hole 250 of the third protrusion 244, and the second mounting piece 226 extends through the center holes 228 of the first protrusion 220 and the second protrusion 222 and the center hole 250 of the third protrusion 244.

The convex block 210 can further include a third recess 224 formed between the first protrusion 220 and the second protrusion 222 for receiving the third protrusion 244 of the concave block 240. Besides, the concave block 240 can have a first recess 246 and a second recess 248 at the two sides of the third protrusion 244 for receiving respectively the first protrusion 220 and the second protrusion 222 of the convex block 210. The match between the first protrusion 220 and the first recess 246, the second protrusion 222 and the second recess 248, and the third protrusion 244 and the third recess 224 helps the second mounting piece 226 support the convex block 210, and enables the convex block 210 to rotate relative to the concave block 240 around the second mounting piece 226. The first protrusion 220 and the second protrusion 222 each have an arcuate profile that matches the first recess 246 and the second recess 248, and the third protrusion 244 has an arc surface that matches the third recess 224.

In addition, the convex block 210 is formed with a first locating slot 216 and a second locating slot 218. Correspondingly, the concave block 240 is formed with a first locating hole 252 and a second locating hole 254 corresponding respectively to the first locating slot 216 and the second locating slot 218. The first locating slot 216 and the second locating slot 218 as well as the first locating hole 252 and the second locating hole 254 have the same radial distance from the center holes 228, 250. However, it will be appreciated that the first locating slot 216 and the second locating slot 218 may have different radial distances from the center hole 228, and that the first locating hole 252 and the second locating hole 254 may have different radial distances from the center hole 250. Respective mounting piece can extend through the first locating hole 252 and the second locating hole 254 to be received in the first locating slot 216 and the second locating slot 218 respectively. The left ends of the first locating slot 216 and the second locating slot 218 define the leftmost position for the rotation of the convex block 210 around the second mounting piece 226 relative to the concave block 240. The right ends of the first locating slot 216 and the second locating slot 218 define the rightmost position for the rotation of the convex block 210 around the second mounting piece 226 relative to the concave block 240.

For assembly of the convex block 210 with the concave block 240, the center hole 228 of the first protrusion 220 and the second protrusion 222 of the convex block 210 is first aligned with the center hole 250 of the third protrusion 244 of the concave block 240. Then, the second mounting piece 226 is inserted through the center holes 228 and 250 to enable the convex block 210 to rotate around the second mounting piece 226 relative to the concave block 240. To support the rotating base 104, the convex block 210 is rotated to a suitable position around the second mounting piece 226 where the first locating hole 252 and the second locating hole 254 are aligned respectively with the first locating slot 216 and the second locating slot 218. Fixing means are inserted through the first locating hole 252 and the first locating slot 216 and through the second locating hole 254 and the second locating slot 218, and fastened. As such, the position of the self adjusting bearing 200 can be adjusted to adapt to the need for supporting the rotating base 104.

Alternatively, although the first locating hole 252 and the second locating hole 254 are formed in the third protrusion 244 of the concave block 240, and the first locating slot 216 and the second locating slot 218 are formed in the first protrusion 220 and the second protrusion 222 of the convex block 210 in the embodiment shown, it is possible for the first locating hole 252 and the second locating hole 254 to be formed in the first protrusion 220 and the second protrusion 222 of the convex block 210, and the first locating slot 216 and the second locating slot 218 to be formed in the third protrusion 244 of the concave block 240. In addition, the number of the locating holes and slots can be other than two.

Alternatively, the structures of the convex block 210 and the concave block 240 can be interchanged such that the third protrusion 244 is formed on the convex block 210, and the first protrusion 220 and the second protrusion 222 are formed on the concave block 240. Accordingly, the first recess 246 and the second recess 248 are formed on the convex block 210, and the third recess 224 is formed on the concave block 240.

Referring again to FIG. 4, the fixed type bearing 300 has a roller 302, a first leg 306, a second leg 308, a seat 310, and a mounting piece 304 for rotatably supporting the roller 302 between the first leg 306 and the second leg 308. The roller 302 contacts the chamfer 122 of the rotating base 104.

Figure 8:
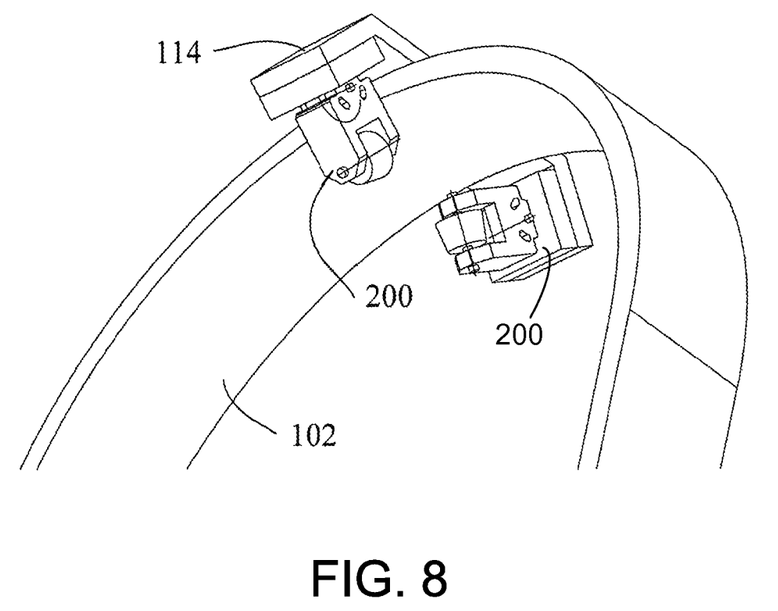
FIG. 8 is a perspective view showing in detail a first bearing couple mounted on an upper part of a main frame of the CT gantry of the CT system.
Figure 9:
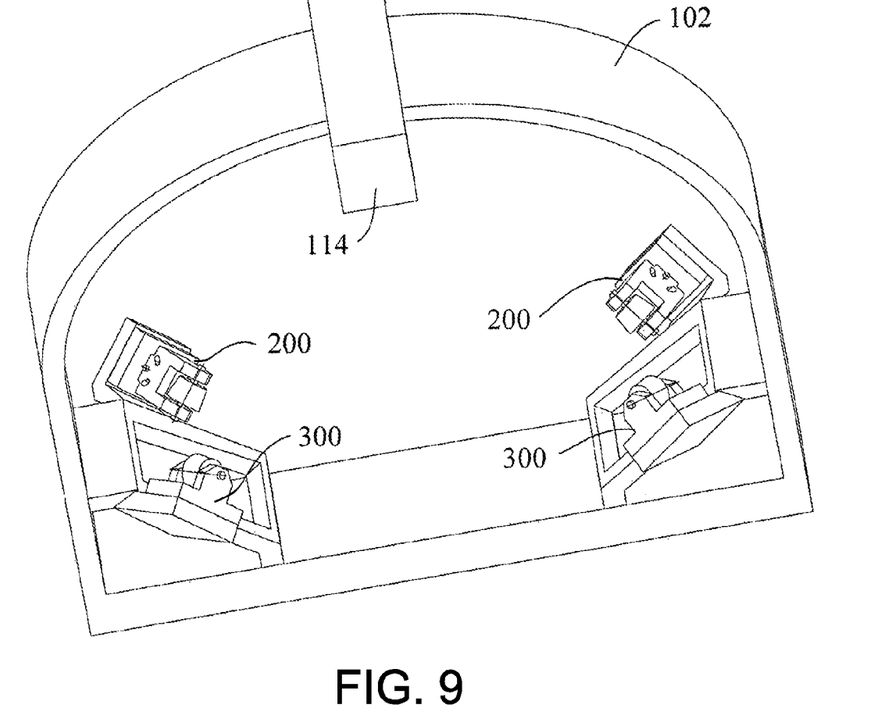
FIG. 9 is a perspective view showing in detail a second bearing couple and a third bearing couple mounted on a lower part of the main frame of the CT gantry of the CT system.

FIG. 8 illustrates self adjusting bearings 200 mounted on an upper part of the main frame 102 of the CT gantry 100, with the two self adjusting bearings 200 disposed at two opposing sides of the main frame 102. FIG. 9 illustrates self adjusting bearings 200 and fixed type bearings 300 mounted on a lower part of the main frame 102 of the CT gantry 100, with the self adjusting bearings 200 disposed at one side of the main frame 102 and the fixed type bearings 300 disposed at an opposite side of the main frame 102.

Figure 10:
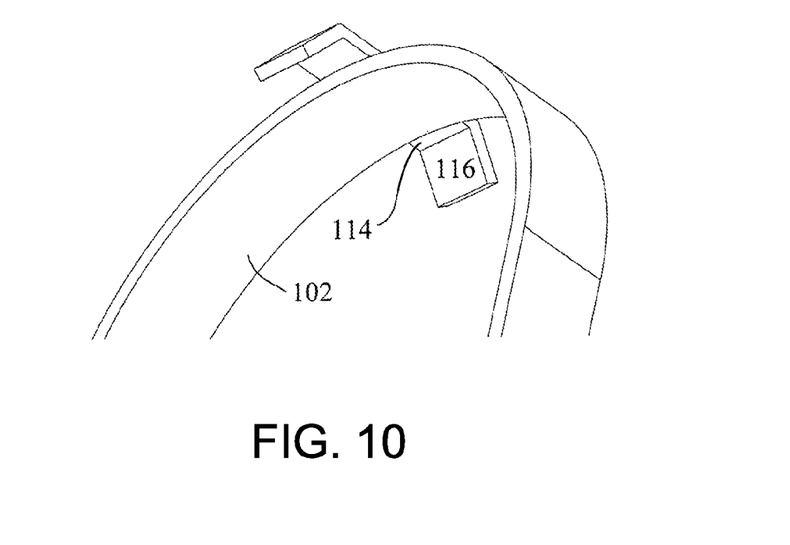
FIG. 10 is a perspective view showing in detail an upper bearing support bracket of the CT gantry.
Figure 11:
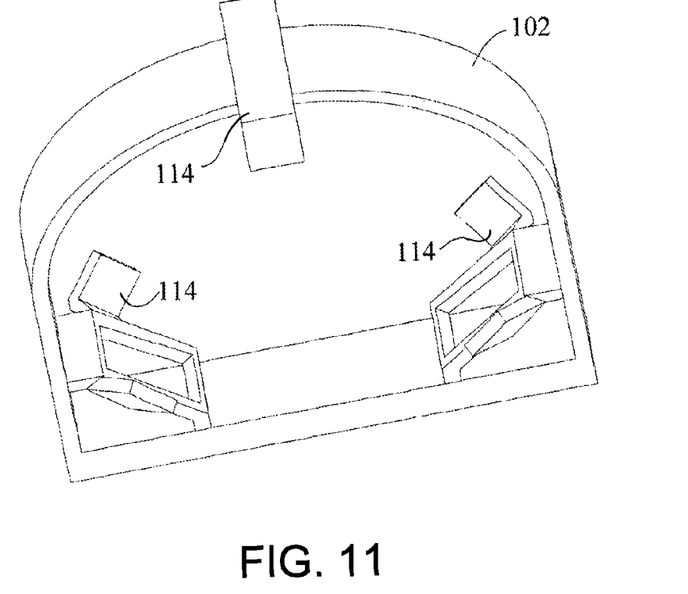
FIG. 11 is a perspective view showing in detail a lower bearing support bracket of the CT gantry.

FIG. 10 and FIG. 11 show three bearing support brackets 114 fixed on the main frame 102 for mounting the first bearing couple 400, the second bearing couple 500, and the third bearing couple 600 respectively. The seats 242 of the self adjusting bearings 200 and the seats 310 of the fixed type bearings 300 are all mounted on the tilting surfaces 116 of the bearing support brackets 114. The bearing support brackets 114 are designed in a way to allow the self adjusting bearings 200 and the fixed type bearings 300 to be mounted onto the rotating base 104 in a desired position and pose.

Figure 12:
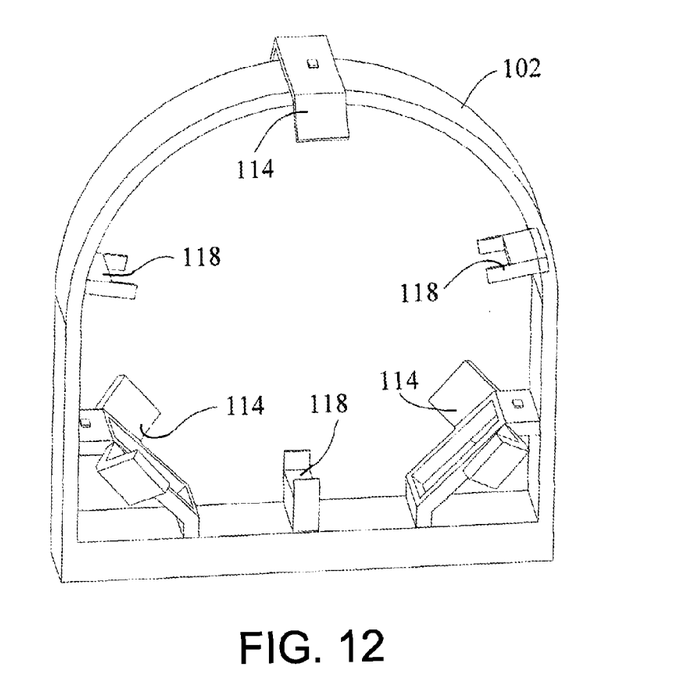
FIG. 12 is a perspective view of failsafe sets of the CT gantry.
Figure 13:
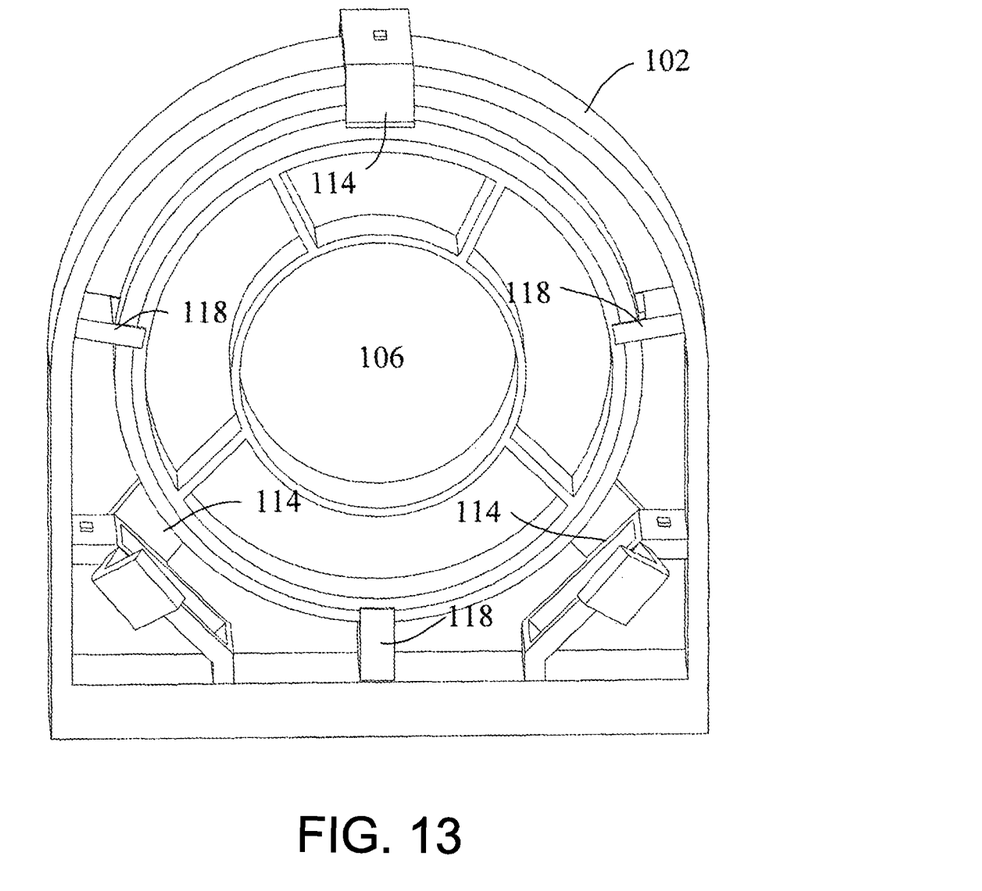
FIG. 13 is a perspective view showing the rotating base supported by the failsafe sets.

FIG. 12 shows failsafe sets 118 of the CT gantry 100. The failsafe sets 118 are designed to support the rotating base 104 when the self adjusting bearings 200 and the fixed type bearings 300 fail, as shown in FIG. 13. There are three failsafe sets 118 which are disposed between the first bearing couple 400, the second bearing couple 500, and the third bearing couple 600.

In addition, the CT gantry 100 further includes a sensor for detecting strain or force at special position of the CT gantry 100 and a sensor alarm controller for giving an alarm when detected strain or force exceeds a preset value.

Figure 14:
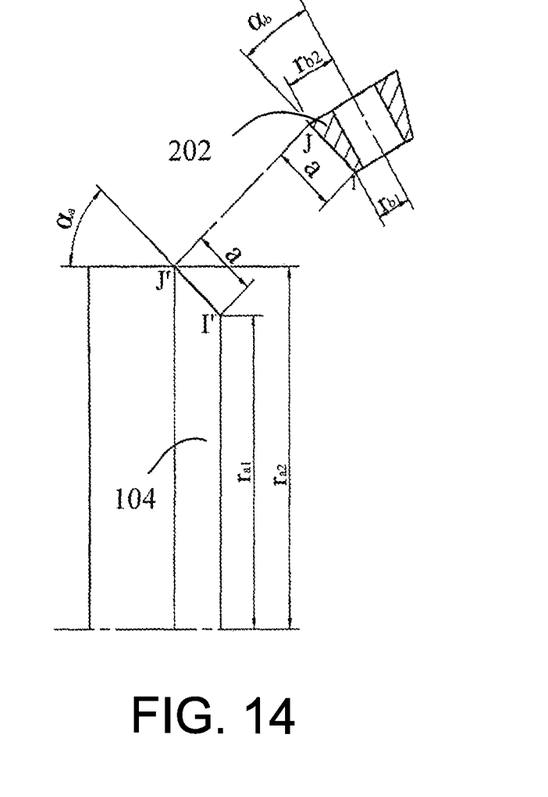
FIG. 14 is a schematic diagram illustrating an angular relationship between the rotating base and the roller of the self adjusting bearing.

Referring again to FIG. 3 and FIG. 4, the rotating base 104 has an outer periphery 120 and a chamfer 122. The outer periphery 120 engages with the driving belt 112, and the chamfer 122 is in contact with the roller 202 of the self adjusting bearing 200 and the roller 302 of the fixed type bearing 300. The rollers 202, 302 are cone shaped in the exemplary embodiment. As shown in FIG. 14, in order to get a roll friction between the rotating base 104 and the self adjusting bearing 200 and the fixed type bearing 300, the cone angle $\alpha_b$ of the rollers 202, 302 and the angle $\alpha_a$ of the chamfer 122 shall comply with the following equation:

$$\sin\alpha_b = \frac{\frac{r_{b1} \cdot (r_{a1} + a \cdot \sin\alpha_a)}{r_{a1}} - r_{b1}}{a},$$

which can be calculated in the following manner:

$$V_{I'} = \omega_1 r_{a1}; \; V_{J'} = \omega_1 r_{a2}$$

$$V_I = \omega_2 r_{b1}; \; V_J = \omega_2 r_{b2}$$

since: $V_{I'} = V_I V_{J'} = V_J$ $$\omega_1 r_{a1} = \omega_2 r_{b1}; \; \omega r_{a2} = \omega_2 r_{b2}$$

$$\frac{\omega_1 r_{a1}}{\omega_1 r_{a2}} = \frac{\omega_2 r_{b1}}{\omega_2 r_{b2}} \Rightarrow \frac{r_{a1}}{r_{a2}} = \frac{r_{b1}}{r_{b2}}$$

since: $r_{a2} = (r_{a1} + a \cdot \sin\alpha_a)\; r_{b2} = (r_{b1} + a \cdot \sin\alpha_b)$ then:

$$\frac{r_{a1}}{r_{a1} + a \cdot \sin\alpha_a} = \frac{r_{b1}}{r_{b1} + a \cdot \sin\alpha_b} \Rightarrow \sin\alpha_b$$

$$= \frac{\frac{r_{b1} \cdot (r_{a1} + a \cdot \sin\alpha_a)}{r_{a1}} - r_{b1}}{a}$$

where:

$V_{I'}$ is the linear speed of point I' of rotating base 104; $V_{J'}$ is the linear speed of point J' of rotating base 104;

$V_I$ is the linear speed of point I of roller 202, 302; $V_J$ is the linear speed of point J of roller 202, 302;

$\omega_1$ is the angular velocity of rotating base 104; $\omega_2$ is the angular velocity of self adjusting bearing 200 and fixed type bearing 300.

Figure 15:
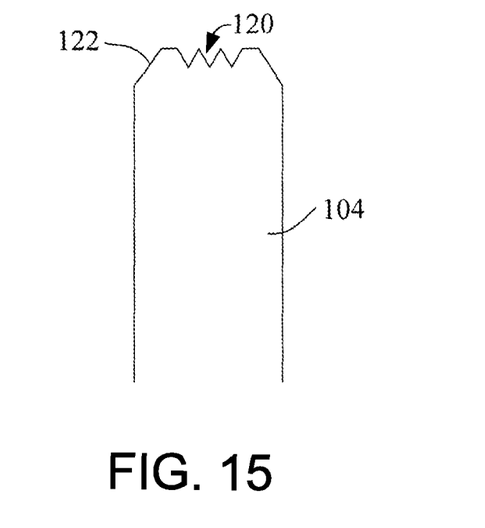
FIG. 15 is a schematic view showing a chamfer and an outer periphery of the rotating base.

FIG. 15 shows an outer periphery 120 and a chamfer 122 of the rotating base 104. The outer periphery 120 has a driving surface with slots or teeth for engagement with driving belt 112 for driving the rotating base 104. The chamfer 122 is in touch with the roller 202 of the self adjusting bearing 200 and the roller 302 of the fixed type bearing 300, severing as a guide rail for guiding the self adjusting bearing 200 and the fixed type bearing 300. Besides, other rotating components in the CT gantry 100 are assembled and fixed on the rotating base 104.

Although this present invention has been described in connection with a limited number of embodiments, it shall be readily understood that the present invention is not restricted to these embodiments. Rather, the present invention can be altered to include any number of changes, modifications, substitutions, or equivalent arrangements not described above but are within the spirit or scope of the present invention. In addition, although various embodiments of the present invention are described, it shall be appreciated that aspects of the present invention may include only some of these described embodiments. Thus, the present invention shall not be construed as limited by the foregoing description. Rather, the present invention is limited by the scope of the appended claims.

The invention claimed is:

1. A self adjusting bearing for use on a CT gantry, said self adjusting bearing configured to be mounted on a main frame of the CT gantry and configured to support a rotating base of the CT gantry, wherein:
    said self adjusting bearing comprises a roller, a first component, and a second component;
    said roller is configured to support said rotating base and is rotatably mounted on said first component;
    said second component is configured to be mounted on the main frame;
    said first component and said second component are configured to rotatably engage each other such that they can rotate relative to each other during the mounting of said self adjusting bearing;
    one of said first component and said second component comprises a convex block, and the other of said first component and said second component comprises a concave block;
    said convex block comprises a first protrusion, a second protrusion, and a third recess therebetween;
    said concave block comprises a first recess, a second recess, and a third protrusion therebetween;
    said first protrusion and said second protrusion are configured to be received in said first recess and said second recess, respectively; and
    said third recess is configured to receive said third protrusion of said concave block.

2. The self adjusting bearing according to claim 1, wherein an axis of rotation of said first component is one of perpendicular to and parallel to an axis of rotation of said roller.

3. The self adjusting bearing according to claim 1, wherein:
    a first leg and a second leg are provided at an upper end of said first component; and
    said roller is rotatably mounted between said first leg and said second leg around a first mounting piece.

4. The self adjusting bearing according to claim 3, wherein:
    said first protrusion, said second protrusion, and said third protrusion each extend one of approximately perpendicular to and approximately parallel to said first leg and said second leg.

5. The self adjusting bearing according to claim 1, wherein:
    said first protrusion and said second protrusion each have an arcuate profile similar to an arcuate profile of said first recess and said second recess; and
    said third protrusion has an arcuate profile similar to an arcuate profile of said third recess.

6. The self adjusting bearing according to claim 1, wherein:
    a mounting piece extends through said first protrusion, said second protrusion, and said third protrusion; and
    said convex block and said concave block are configured to rotate relative to each other around said mounting piece.

7. The self adjusting bearing according to claim 1, wherein:
    said first protrusion and said second protrusion each comprise a locating slot;
    said third protrusion comprises a locating hole;

a fixing means extends through said locating hole and is configured to be slidably received in said locating slot; and a relative position of said convex block to said concave block is secured when said fixing means is fastened.

8. The self adjusting bearing according to claim 7, wherein:

said locating hole comprises two locating holes having equal radial distance to the axis of rotation of said first component; and said locating slot comprises two locating slots having equal radial distance to an axis of rotation of said first component.

9. The self adjusting bearing according to claim 1, wherein:

said first protrusion and said second protrusion each comprise a locating hole;

said third protrusion comprises a locating slot;

a fixing means extends through said locating hole and is configured to be slidably received in said locating slot; and a relative position of said convex block and said concave block is secured when said fixing means is fastened.

10. The self adjusting bearing according to claim 1, wherein said roller is cone shaped, and a cone angle of said roller is arranged such that said roller has roll friction with said rotating base.

11. A CT system comprising a self adjusting bearing according to claim 1.

12. A CT gantry comprising a main frame, a rotating base, and a self adjusting bearing according to claim 1, wherein said self adjusting bearing is mounted on said main frame and supports said rotating base.

13. The CT gantry according to claim 12, further comprising a fixed type bearing arranged on said main frame and disposed at a side of said rotating base opposite said self adjusting bearing.

14. The CT gantry according to claim 13, wherein said CT gantry comprises a first bearing couple comprising two self adjusting bearings, and a second bearing couple and a third bearing couple each comprising one self adjusting bearing and one fixed type bearing.

15. The CT gantry according to claim 12, wherein said rotating base has a chamfer configured to guide said roller of said self adjusting bearing.

16. The CT gantry according to claim 12, wherein said rotating base comprises a driving surface disposed on an outer periphery, said driving surface engages a driving belt for driving said rotating base.

17. The CT gantry according to claim 12, further comprising a failsafe set mounted on said main frame configured to support said rotating base upon failure of said self adjusting bearing.

18. The CT gantry according to claim 12, further comprising a bearing support bracket mounted on said main frame, said self adjusting bearing mounted on a tilting surface of said bearing support bracket.

19. A CT system comprising a CT gantry according to claim 12.

* * * * *